Figure 1:
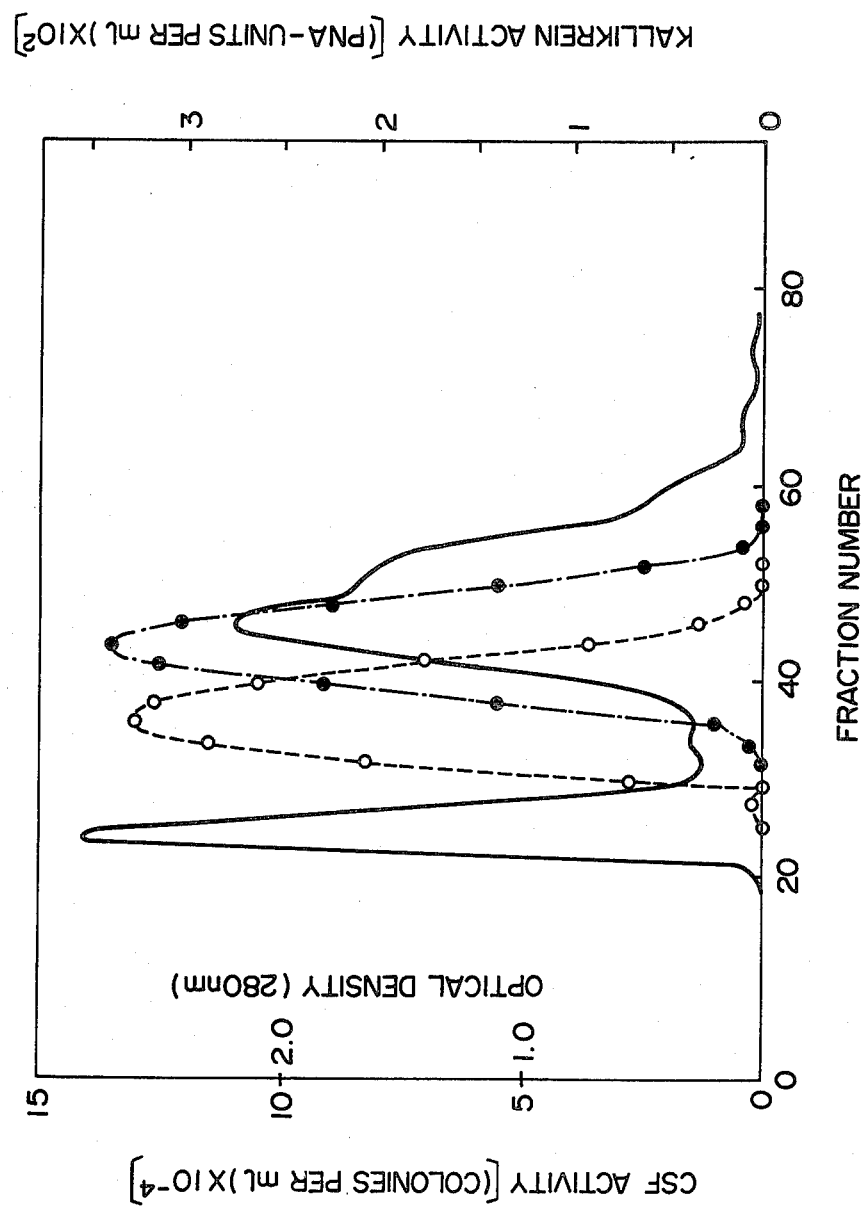

United States Patent [19]

Funakoshi et al.

[11] Patent Number: 4,482,485

[45] Date of Patent: Nov. 13, 1984

[54] METHOD OF PREPARATION OF HUMAN URINE ORIGIN COLONY-STIMULATING FACTOR AND KALLIKREIN

[75] Inventors: Satoshi Funakoshi, Katano; Kazuo Morimoto, Fukuchiyama; Morio Kuboyama; Nobuya Yanai, both of Tokyo; Muneo Yamada, Kawasaki; Hajime Yokota, Tokyo, all of Japan

[73] Assignees: The Green Cross Corp., Osaka; Morinaga Milk Industry Co., Ltd., Tokyo, both of Japan

[21] Appl. No.: 568,259

[22] Filed: Jan. 4, 1984

[30] Foreign Application Priority Data

Jan. 28, 1983 [JP] Japan .................................. 58-11317

[51] Int. Cl.$^3$ ........................ A61K 35/22; C07G 7/00
[52] U.S. Cl. .................................. 260/112 R; 424/99; 424/177; 260/112.5 R; 435/219; 435/226
[58] Field of Search .................... 260/112 R, 112.5 R; 435/219, 226; 424/99, 177

[56] References Cited

U.S. PATENT DOCUMENTS

| | | | |
|---|---|---|---|
| 2,874,088 | 2/1959 | Schultz | 424/99 |
| 3,100,736 | 8/1963 | Werle et al. | 424/99 |
| 3,905,870 | 9/1975 | Kutzbach et al. | 435/226 |
| 4,178,285 | 12/1979 | Feits et al. | 260/112 R |
| 4,252,902 | 2/1981 | Fujii et al. | 435/226 X |
| 4,275,056 | 6/1981 | Takaku et al. | 260/112 R X |
| 4,289,690 | 9/1981 | Pestka et al. | 260/112 R |
| 4,342,828 | 8/1982 | Takaku et al. | 424/99 X |
| 4,359,415 | 11/1982 | Sloane | 260/112 R |
| 4,393,140 | 7/1983 | Schutt | 435/226 |

OTHER PUBLICATIONS

Blood, 52, 1012–1020 (1978), Motoyoshi et al.
Blood, 58, 630–641 (1981), Das et al.
Japanese Journal of Medicine, 21, 187–191 (1982), Motoyoshi et al.
Anal. Biochem. 48, 1839 (1976), Chang et al.

*Primary Examiner*—Howard E. Schain
*Attorney, Agent, or Firm*—Cushman, Darby & Cushman

[57] ABSTRACT

Human urine-origin colony-stimulating factor and kallikrein are separated in pure form, respectively, from an aqueous solution thereof, such as a urinary protein-concentrated solution by subjecting the solution added with a stabilizer such as octyl-phenoxypolyethoxyethanaol or polyethylene glycol both having a molecular weight of 1,000–10,000, to high-performance gel filtration effective in molecular exclusive limit of $10^5$–$5\times10^5$ as determined with globular protein.

4 Claims, 2 Drawing Figures

METHOD OF PREPARATION OF HUMAN URINE ORIGIN COLONY-STIMULATING FACTOR AND KALLIKREIN

This invention relates to a method of preparation of human urin origine colony-stimulating factor (hereinafter referred to as CSF) and kallikrein.

More particularly, it relates to a method of simultaneous preparation of kallikrein-free CSF and kallikrein suitable for pharmaceutical use by isolating CSF and kallikrein, which are physiologically active substances, in purified states with high recoveries, from urine of normal humans or a solution containing CSF and kallikrein (hereinafter referred to as "human urine etc.").

CSF and kallikrein are high molecular and physiologically active substances present in trace amounts in human urine. CSF is a glycopretein which acts on granulopoietic stem cells in mouse and human bone marrow and stimulates the proliferation and differentiation of said cells to form monocytes-macrophages and granulocytes which are the constituent cells of the leukocyte [Motoyoshi K. et al., Blood, 52, 1012–1020 (1978); Das S. K. et al., Blood, 58, 630–641 (1981)]. It is also known that CSF stimulates also the in vivo production of CSF by and, when administered to a cancer patient suffering from serious leukopenia due to treatments such as administration of carcinostatic substances of X-ray irradiation, promotes the recovery or increase of the number of leukocytes, of which the granulocyte is the main constituent [Motoyoshi K. et al., Japanese Journal of Medicine, 21, 187–191 (1982).]

On the other hand, kallikrein is a kind of proteolytic enzyme which participates in the formation of kinin which is a physiologically active peptide derived from kininogen present in mammalian plasma, and in blood coagulation system. The kinin formed by kallikrein have such physiological activities as vasodilation of peripheral blood vessels and raising of blood vessel permeability; kallikrein fulfills the function of regulating these activities. Presently, pharmaceutical preparations of kallikrein extracted from animal pancreas are available commercially as a medicine for improving blood circulation or the like. The human urine origin kallikrein has a physiological effect equivalent to those of these animal origin kallikreins, and moreover, because of its being human origin, the human urine origin kallikrein preparation is less liable to lead to side effects caused by foreign proteins, enabling repeated administration, and hence rather more valuable as pharmaceuticals than the animal origin kallikrein preparations.

On the other hand, if pharmaceutical preparations are prepared by isolating CSF and kallikrein from human urine, the contamination of one of the two substances into the pharmaceutical preparation of another is undesirable from the viewpoint of quality and safety of the pharmaceutical. Especially, when CSF is used as a therapeutic agent for granulocytopenia, it is effective to apply it intravenously, and hence the contamination by kallikrein is absolutely unallowable. Because if kallikrein is, even in a very small amount, administered intravenously, it exerts a marked depressive action owing to the peripheral blood vessel-vasodilating action thereof; consequently when a large amount of kallikrein, depending on the administered amount of CSF, is introduced in the vein, it could cause shock on the patient due to a rapid depression of the blood pressure.

Both human urine origin CSF and kallikrein are, as mentioned above, highly valuable as pharmaceuticals. Accordingly, it is very advantageous for the purpose of providing highly safe and low-priced pharmaceuticals to recover them effectively from human urine etc. and prepare them in a completely separated state from each other. However, very little information has hitherto been available as to the method of effectively obtaining the two substances, CSF and kallikrein, separately from each other out of human urine etc. The reason is that although CSF and kallikrein are not always in common with each other in respect to physiological actions and origins thereof, they have closely similar properties. For example, CSF and kallikrein are both a protein having a saccharide chain linked thereto, and the isoelectric points thereof are both in the acid range of pH 3.0–4.5, so that it was difficult to separate them based on the difference of their electric properties. Moreover, when present in human urine, they have molecular weights extremely close to each other, that of CSF being 60,000–100,000 dalton and that of kallikrein being 50,000–80,000 dalton.

Previously, methods of separating and purifying CSF or kallikrein from human urine were studied, as in other physiologically active substances, for each individual substance, and hence these methods were unapplicable to an effective and simultaneous purification of CSF and kallikrein. Consequently, when CSF was prepared in a purified form free from kllikrein, the recovery of kallikrein was very poor. On the other hand, when the isolation of kallikrein was intended, the recovery of CSF was impossible. As to a method of obtaining CSF and kallikrein simultaneously from human urine in a completely separated and purified form with a high percentage of recovery, the present inventors have already invented a method to use affinity chromatography and ion exchanger chromatography, and applied for a patent (Japanese patent application Kokai No. 58629/82; hereinafter referred to as "the method of the prior application").

The method of the prior application can, however, be not in every respect regarded as an ideal one. For example, although the affinity chromatography is excellent in separation characteristics and the cost of the affinitive adsorvent per unit amount to be processed is high. On the other hand, the ion exchanger, although very advantageous economically, has a drawback in its operability and, especially in the case of concentration gradient elution aimed at precise fractionation, needs a moderate processing requiring the greatest possible care and a long time. A third method to isolate CSF and kallikrein simultaneously in purified state is the gelfiltration chromatography wherein fractionation is achieved based on the difference of molecular weight. However, the soft gel widely used hitherto, which is mainly polysaccharide or various plastics, could not effect a complete separation of CSF and kallikrein because of the close proximity of their molecular weights.

The high-performance liquid chromatography is a technique which has been recently developed resulting from the efforts to improve further the various kinds of chromatography widely used for separation and identification of organic compounds. Its feature is to enable, under a high pressure and at a high rate of flow, extremely precise chromatographic fractionation of various compounds in a short time. Especially in the field of gel filtration, it has come to provide a means for improving drastically the fractionation of high molecular substances based on their molecular weights, accompanied by the development of hard gel having excellent pressure resistance to be used in place of the prior soft gel.

The present inventors have perceived the excellent fractionation characteristics of gel filtration in high-performance liquid chromatography and carried out the simultaneous purification of human urine origin CSF and kallikrein using the method. As a result, it was found that CSF and kallikrein could be separated with excellent results on a high-performance liquid chromatography which used a pressure-resistant gel consisting mainly of silica gel. But, commercially available gels for high-performance liquid chromatography showed a nonspecific adsorption phenomenon of CSF and kallikrein thereon, and a portion of each of CSF and kallikrein remained on the gel surface. Although the nonspecific adsorption on gel surface was a phenomenon generally observed in commercial gels, it was possible to prevent the phenomenon by increasing ionic strength of the chromatographic solvent. But the increased ionic strength, on the other side, gave rise to the result that biological activity (hereinafter referred to simply as activity) of CSF became unstable and the amount of activity recovered decreased.

The present inventors made extensive studies on the conditions for high-performance liquid gel filtration to separate and purify CSF and kallikrein effectively, preventing the nonspecific adsorption on the gel as well as the decrease of CSF activity. As a result, this invention has been achieved through the finding that octylphenoxypolyethoxyethanol (hereinafter referred to as OPPE) or polyethylene glycol known as a stabilizer for CSF activity suited to the purpose.

The object of this invention is to provide a method of preparing CSF and kallikrein simultaneously in a completely separated state from each other with high recoveries out of human urine etc.

According to the present invention there is provided a method of preparation of human urine origin colony-stimulating factor and kallikrein, respectively, which comprises concentrating urine of normal humans or a solution containing human urine origin colony-stimulating factor and kallikrein with respect to proteins contained therein, equilibrating the resulting concentrated liquid with a buffer solution containing a stabilizer, subjecting the liquid to high-performance gel filtration chromatography by introducing the liquid into a column which has been filled with a gel having a molecular exclusive limit of $10^5$–$5 \times 10^5$ daltons as determined with globular protein and equilibrated with said buffer solution to fractionating the colony-stimulating factor fractions and kallikrein fractions, and collecting the both.

Figure 2:
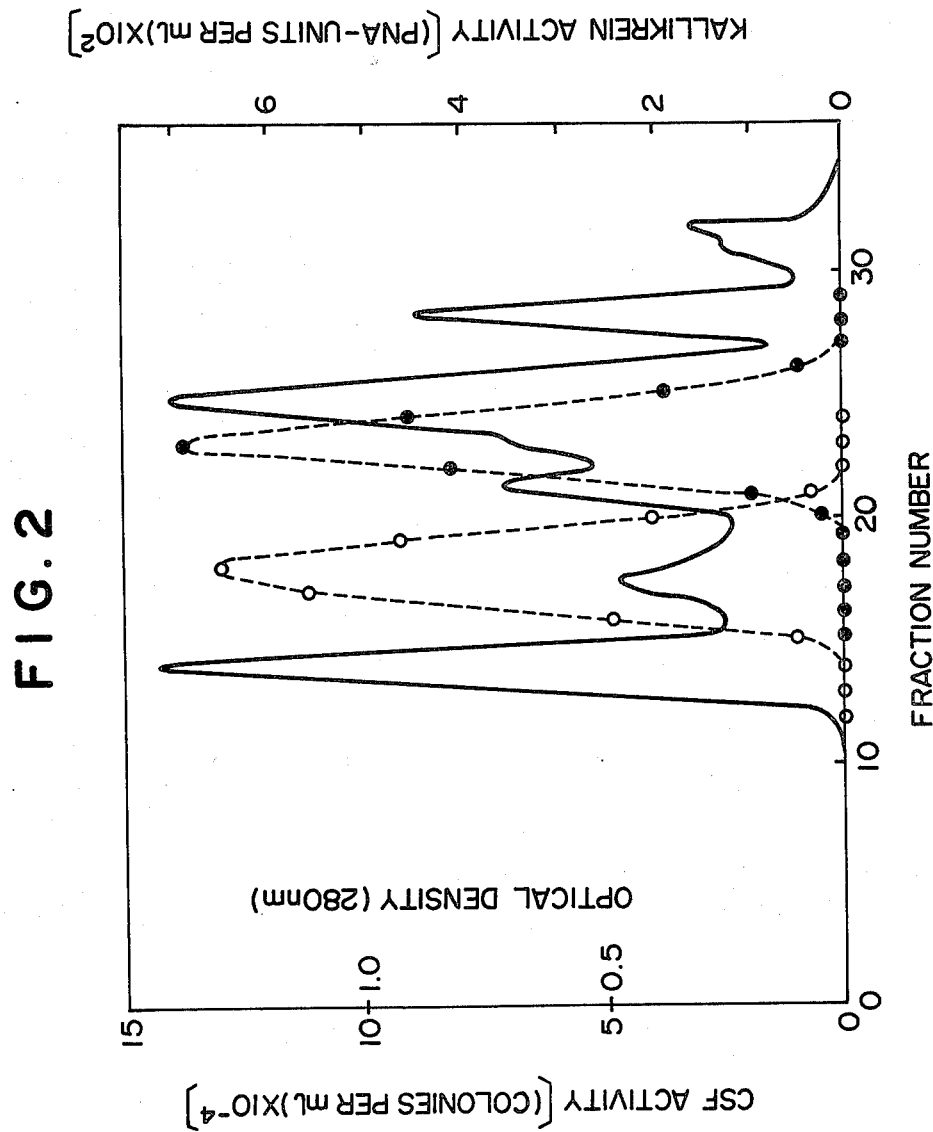

FIGS. 1 and 2 are graphs showing fractionation patterns of CSF and kallikrein by gel filtration according to the prior method and by high-performance gel filtration according to the present invention, respectively. In both Figures, are plotted as the left-hand ordinate the CSF activity and the optical density at 280 nm; as the right-hand ordinate the kallikrein activity; and as the abscissa the fraction number. The symbols —, —o—, and —.— indicate the optical density, CSF activity, and kallikrein activity, respectively.

Human urine etc. are adjusted to pH 6–8 with a dilute acid solution or alkaline solution and concentrated by a suitable known method of concentrating protein including, for example, adsorption on an inorganic adsorbent such as silica gel or an ion exchanger, salting out by the use of a neutral salt such as ammonium sulfate, ultrafiltration, and combination thereof. The content of protein in the resulting concentrated human urine etc. is preferably 2 to 10% (w/v).

The symbol "% (w/v)" or "% (v/v)" referred to in the specification means the amount of a material by weight (gram) or by volume (ml) in 100 ml of the liquid, respectively.

For a further advantageous practicing of this invention, some known methods may be used, in the above concentration step, to remove as much contaminating high molecular substances as possible within a range not deleterious to the recovery of CSF and kallikrein.

The thus concentrated liquid is equilibrated with a buffer solution having an ionic strength of at least 0.05 and less than 0.5, preferably 0.1–0.3 and a pH of 6.0–8.0, for example, sodium phosphate buffer solution Then, OPPE, for example Triton X-100 (trade name, made by Rohm & Haas Co.) or polyethylene glycol both having a molecular weight of 1,000–10,000 is added thereto as a stabilizer to a concentration of 0.01–0.1% (w/v). Then, the resulting liquid is subjected to a high-performance gel filtration by injecting it into a column filled with a gel for high-performance liquid chromatography having a molecular exclusive limit of $10^5$–$5 \times 10^5$ dalton as determined with globular protein, such as commercially available TSK-Gel 3000 SW (trade name, mfd. by Toyo Soda Inc.) ZORBAX PSM-1000 (trade name, mfd. by DuPont Inc.), or Shim-pack HSG-40 (trade name, mfd. by Shimazu Seisakusho Inc.) and equilibrated with above-mentioned buffer solution containing the same amount of the stabilizer by passing the solution through it beforehand; and by passing said liquid through said column in a rate of 1 to 5 ml·cm$^{-2}$·min$^{-1}$ by means of a high pressure pump. The pressure of the buffer solution passing through the column is varied depending on the radius of the column, but is normally preferably 10 kg/cm$^2$ or higher for a diameter of 5 mm.

By the procedures mentioned above, are eluted from the column CSF as a fraction having a single peak at a molecular weight of 85,000 dalton, and kallikrein as a fraction having a peak at a molecular weight of 60,000 dalton to be recovered individually. The CSF and kallikrein are respectively, as desired, subjected to dialysis and desalting, mixed with a pharmaceutically acceptable pH-adjusting salt, solubilizing aid or excipient, and then subjected to a treatment such as membrane filtration for sterilization and filling or aseptical lyophilization to give a pharmaceutical. The CSF and kallikrein separated in the above-mentioned manner can also be further purified individually by known methods.

Thus, CSF and kallikrein are prepared simultaneously.

This invention is illustrated in detail below with reference to Test Examples and Examples.

TEST 1

Comparative test of gel filtration chromatography of this invention with that of prior method A concentrated liquid from human urine prepared in the same manner as in Example 1 described later was subjected to gel filtration chromatography by using Sephacryl S-300 (trade name, mfd. by Pharmacia Fine Chemicals Inc.) of the prior method and TSK-Gel 3000 SW (trade name, mfd. by Toyo Soda Inc.) for high-performance liquid chromatography of this invention to compare the separation characteristics of the two methods. Into the Sephacryl S-300 column ($\phi 20 \times 1200$ mm) was injected 1.4 ml of said concentrated liquid, and into the TSK-Gel 3000 SW column ($\phi 7.5 \times 1200$ mm) was injected 0.2 ml of the same liquid. Chromatography was carried out by passing the same buffer solution as in Example 1 at a flow rate of, in the former column, 5 ml/cm$^2$/hr by the use of a perista pump and, in the latter column, 2.0 ml/cm$^2$/min by the use of a high-pressure liquid-conveying pump LC-3A (mfd. by Shimazu Seisakusho Inc.). Fractions of 5 ml each (in the former) or 2 ml each (in the latter) were collected and examined for CSF and kallikrein activities thereof by the following method of determination.

The CSF activity was determined according to colony formation method by the use of the monolayer soft agar culture technique employing the C$_{57}$BL/6N mouse bone marrow cell. Thus, each fraction sample was suitably diluted with distilled water containing 2% (v/v) of bovine serum and sterilized by filtration (using 0.45 $\mu$ pore filter). Each 0.1 ml portion of the filtrate was placed in three Petri dishes and 1 ml of Mc Coy's 5A medium containing 0.3% (w/v) of agar, 20% (v/v) of fetal calf serum, and $1 \times 10^5$ C$_{57}$BL/6N mouse bone marrow cells was added thereto. After thorough mixing, the mixture was incubated for 7 days in an incubator at 37° C. in a fully humidified 7.5% (v/v) of carbon dioxide atmosphere. After incubation, the number of colonies formed was counted under a microscope, the term "colony" herein meaning a cell aggregate containing more than 50 cells. The CSF activity was expressed in terms of the number (units) of colonies formed. One "unit" herein means one colony formed. The purity of the CSF specimen obtained was expressed in terms of specific activity, which indicated the number of colonies formed per 1 mg of the protein specimen.

The kallikrein activity was determined by an enzymochemical method using H-D-Val-Leu-Arg-paranitroaniline (hereinafter referred to as "peptide-PNA"), a synthetic substrate of kallikrein. Thus, 0.1 ml of the sample was mixed with 2 ml of a 0.2 M tris-HCl buffer solution (pH 8.0), preincubated at 37° C. for 5 minutes, then mixed with 0.2 ml of 0.2 mM solution of the peptide-PNA, and allowed to react at 37° C. for 30 minutes. Then, 0.2 ml of 50% (w/v) acetic acid solution was added to the reaction mixture to terminate the reaction, and the amount of PNA liberated was measured at a wave length of 405 nm. A sample containing aprotinine, an inhibitor against kallikrein, was used as the control. The kallikrein activity was expressed in terms of the amount of PNA formed per 1 minute at 37° C. Namely, 1 "PNA unit" means 1 $\mu$mole of PNA formed in 1 minute.

The separation patterns in the prior method and in high-performance liquid chromatography according to this invention were as shown in FIG. 1 and FIG. 2, respectively.

FIGS. 1 and 2 are graphs showing fractionation patterns of CSF and kallikrein by the prior method and by the method of this invention, respectively. In both Figures, are plotted as the left-hand ordinate the CSF activity and the optical density at 280 nm; as the righthand ordinate the kallikrein activity; and as the abscissa the fraction number. The symbols —, —o—, and —●— indicate the optical density, CSF activity and kallikrein activity, respectively.

In the gel filtration chromatography using Sephacryl S-300 according to the prior method, CSF and kallikrein were not separated completely from each other, and the recovery of CSF fraction free from kallikrein was less than 30%. On the contrary, in the high-performance liquid chromatography according to the method of this invention, CSF and kallikrein were separated nearly completely from each other, and the recovery of CSF free from kallikrein was 90% or more; thus, contamination by kallikrein was substantially nil. The results of determination of percentage of recovery of CSF and kallikrein as well as the amount of contaminating kallikrein in CSF in both of the above methods are as shown in Table 1.

TABLE 1

| | Recovery of CSF and kallikrein by the prior method and the method of this invention | | |
|---|---|---|---|
| | CSF fraction | | |
| | Recovery (%) | Amount of contaminating kallikrein (PNA unit) | Kallikrein recovery (%) |
| Sephacryl S-300 | 26.5 | 0.0019 | 38 |
| Method of this invention | 92.5 | 0.0001≧* | 90 |

Note:
*It means the amount is below the detection limit of the method used.

TEST 2

Comparison of recoveries under varied conditions of the ionic strength of buffer solution and of the concentration of stabilizer In order to investigate the adsorption phenomenon of CSF and kallikrein upon the gel filtration carrier for high-performance liquid chromatography as well as the effects of the ionic strength of buffer solution and the concentration of stabilizer, high-performance liquid chromatography was carried out under varied conditions, and the CSF and kallikrein activities were determined in the same manner as in Test 1 to compare the recoveries.

The human urine concentrated liquid used in the test was prepared in the same manner as in Example 1. The high-performance liquid chromatography was carried out by the use of TSK-Gel 3000 SW column ($\phi 7.5 \times 1200$ mm) and LC-3A pump at room temperature and at a flow rate of 1 ml/min.

The stabilizer used was polyethylene glycol (made by Sigma Co.; average molecular weight: 6,000 dalton), and the buffer solutions used were those containing 0.01 M-0.5 M of sodium phosphate and having a pH of 7.0 (ionic strength: about 0.02–1.14). The test results were as shown in FIG. 2 and Table 3. When chromatography was carried out by using buffer solution of various concentrations containing no stabilizer, the recovery was low with any of the buffer solutions of various concentrations. Especially when the ionic strength was low, both the recovery of CSF and that of kallikrein were low.

TABLE 2

| Concentration of the buffer solution containing no stabilizer vs. recoveries* of CSF and kallikrein | | |
|---|---|---|
| Concentration of sodium phosphate (M) | CSF recovery (%) | Kallikrein recovery (%) |
| 0.01 | 20.6 | 59.8 |
| 0.05 | 38.3 | 60.8 |
| 0.1 | 42.9 | 84.6 |
| 0.2 | 40.3 | 81.3 |

TABLE 2-continued

Concentration of the buffer solution containing no stabilizer vs. recoveries* of CSF and kallikrein

| Concentration of sodium phosphate (M) | CSF recovery (%) | Kallikrein recovery (%) |
|---|---|---|
| 0.3 | 39.5 | 80.5 |
| 0.4 | 29.6 | 79.4 |
| 0.5 | 28.8 | 81.8 |

Note:
*Percentage of recovery based on the activity of the concentrated liquid before treatment On comparative examination of recoveries of CSF obtained by using 0.1 M sodium phosphate buffer solution (ionic strength 0.20) containing polyethylene glycol or Triton X-100 at various concentrations indicated in Table 3 below, it was revealed that the recovery of CSF was markedly improved when polyethylene glycol or Triton X-100 was used at a concentration of 0.01–0.1% as the stabilizer. The stabilizer is used preferably at a lower concentration. As shown in Table 3, a concentration of 0.01% (w/v) of the stabilizer gave nearly satisfactory results. Since a higher concentration of the stabilizer than that required gave rise to incomplete separation between CSF and kallikrein and increased the viscosity of the sample, concentrations over 0.1% (w/v) were not preferable.

TABLE 3

CSF recoveries by the use of buffer solution of various concentrations of stabilizer

| Stabilizer concentration (%) (w/v) | CSF recovery (%) | |
|---|---|---|
| | Polyethylene glycol | Triton X-100 |
| 0 | 40.3 | 40.3 |
| 0.005 | 72.6 | 68.2 |
| 0.01 | 88.4 | 90.6 |
| 0.05 | 92.4 | 91.8 |
| 0.1 | 94.5 | 93.4 |
| 0.5 | —* | —* |

Note:
*Incomplete separation between CSF and kallikrein

Although the results shown in Table 3 were obtained with 0.2 M sodium phosphate buffer solution (pH 7), even when the ionic strength of the buffer solution was regulated by addition of a neutral salt such as sodium chloride, a similar improvement in recovery was observed when the stabilizer was present. The results were as shown in Table 4, which compared the recoveries of CSF and kallikrein obtained with various buffer solutions in the presence of 0.01% of polyethylene glycol.

TABLE 4

Recovery of CSF and kallikrein with various buffer solution

| Buffer solution | CSF recovery (%) | Kallikrein recovery (%) |
|---|---|---|
| 0.1 M NaCl + 0.02 M sodium phosphate (pH 70.0) | 90.8 | 92.4 |
| 0.2 M KCl + 0.01 M tris-HCl (pH 7.0) | 91.2 | 92.8 |

The pH of the buffer solution used in chromatography does not affect in itself the separation characteristics for CSF and kallikrein. But if it is in alkaline range and a gel consisting mainly of silica gel is used, the dissolution of the gel occurs; if it is in acid range the corrosion of the apparatus such as the column may take place. Accordingly, the most favorable pH is in a nearly neutral range, pH 6.0–8.0.

EXAMPLE 1

About 20 l of human urine was adjusted to pH 7.0 with 10 N NaOH solution, passed through a silica gel column ($\phi$ 4.0×50 cm) to adsorb the protein constituent therein on the column. The column was then eluted with 500 ml of 5% aqueous ammonia solution. The eluate was neutralized with 1 N $H_2SO_4$ and then centrifuged at 10,000 r.p.m. for 30 minutes to remove the insolubles. The resulting eluate was then mixed with ammonium sulfate to a 70% saturation to form a precipitate, and centrifuged at 4° C. and 10,000 r.p.m. for 30 minutes to collect the precipitate. The precipitate thus obtained was dissolved in 100 ml of a 0.02 M phosphate buffer solution, and further diluted ten-fold with the same buffer solution. To the resulting solution was added 40 g of DEAE-cellulose which had been equilibrated with said buffer solution beforehand, and the two was mixed at 4° C. for 1 hour. After mixing, the DEAE-cellulose was collected by filtration, washed thoroughly with a 0.02 M phosphate buffer solution and said buffer solution containing 0.1 M NaCl, and then eluted with 500 ml of 0.02 M phosphate buffer solution containing 0.4 M NaCl. The eluate was filtered through a glass filter, then concentrated by means of an ultrafiltration membrane (HC-1, mfd. by Asahi Kasei Inc.) and at the same time equilibrated with 0.1 M phosphate buffer solution, to give a concentrated liquid of human urine.

To 20 ml of the concentrated liquid thus obtained [protein concentration 4.2% (w/v)], was added Polyethylene Glycol 6000 (made by Sigma Co.) to a concentration of 0.01% (w/v), and the mixture was filtered through a 0.4 $\mu$ pore filter.

The resulting human urine concentrated liquid (0.2 ml) was injected into a column ($\phi$7.5×1200 mm) filled with TSK-Gel 3000 SW and equilibrated beforehand with 0.1 M phosphate buffer solution (pH 7.0) containing 0.01% (w/v) of polyethylene glycol, and subjected to high-performance liquid chromatography by passing the above buffer solution through the column at a flow rate of 1.0 ml/min with a high pressure pump, to separate CSF and kallikrein. Ten ml each of CSF and kallikrein fraction were recovered, desalted by dialysis and then lyophilized aseptically, to give about 1 mg of CSF and about 2.4 mg of kallikrein. The recovery in terms of activity of CSF obtained was about 94% based on the starting material (human urine); the specific activity of the CSF obtained had been elevated to $4 \times 10^5$ units/mg protein; and no contamination of kallikrein therein was observed at all. On the other hand, the recovery in terms of activity of kallikrein obtained was about 78% and the specific activity was 0.325 PNA units/mg protein.

EXAMPLE 2

Twenty liters of urine of normal humans was equilibrated with 0.02 M phosphate buffer solution (pH 7.4) by using an ultrafiltration membrane (HIOPIO, mfd. by Amicon Corp.), and 40 g of DEAE-cellulose equilibrated with above buffer solution beforehand was added thereto. After mixing at 4° C. for 1 hour, the DEAE-cellulose was collected by filtration. The DEAE-cellulose was washed thoroughly with said buffer solution and then eluted with 1 l of 0.02 M phosphate buffer solution (pH 7.4) containing 0.4 M NaCl to give a concentrated liquid of human urine. The concentrated liquid obtained was further concentrated by means of an ultrafiltration membrane, dialyzed against a 0.1 M phosphate buffer solution (pH 7.0) containing 0.01% (w/v) of Triton X-100, then injected into a TSK-Gel 3000 SW column equilibrated beforehand with said buffer solution, and thereafter processed in the same manner as in Example 1, to give about 0.9 mg of CSF and about 2.5 mg of kallikrein. The recoveries in terms of activity of CSF and kallikrein obtained were 92% and 94%, respectively.

Effect of the Invention

The effects which can be achieved by the method of this invention are as follows:
(1) The recoveries of CSF and kallikrein are respectively about 3.5 and about 2.5 times that in the prior method.
(2) CSF and kallikrein can be prepared simultaneously.
(3) The CSF obtained is substantially not contaminated by kallikrein.
(4) CSF and kallikrein can be prepared in a far shorter time than in the prior method.

What is claimed is:

1. A method of preparation of human urine origin colony-stimulating factor and kallikrein, respectively, which comprises concentrating urine of normal humans or a solution containing human urine origin colony-stimulating factor and kallikrein with respect to proteins contained therein, equilibrating the resulting concentrated liquid with a buffer solution containing a stabilizer, subjecting the liquid to high-performance gel filtration chromatography by introducing the liquid into a column which has been filled with a gel having a molecular exclusive limit of $10^5 - \times 10^5$ as determined with globular protein and equilibrated with said buffer solution to fractionating the colony-stimulating factor fractions and kallikrein fractions, and collecting the both.

2. A method for preparation according to claim 1, wherein said buffer solution has an ionic strength of 0.05–0.5 and a pH of 6.0–8.0, and contains 0.01–0.1% (w/v) of a stabilizer.

3. A method of preparation according to claim 1, wherein the stabilizer is octyl-phenoxypolyethoxyethanol or polyethylene glycol both having a molecular weight of 1,000–10,000 daltons.

4. A method of preparation according to claim 1, wherein the amount of the stabilizer contained is 0.01–0.1% (w/v) based on the buffer solution.

* * * * *